(12) United States Patent
Heo et al.

(10) Patent No.: US 9,636,071 B2
(45) Date of Patent: May 2, 2017

(54) INTRAORAL SENSOR

(71) Applicants: Rayence Co., Ltd., Gyeonggi-do (KR);
Vatech Ewoo Holdings Co., Ltd.,
Gyeonggi-do (KR)

(72) Inventors: Sung Kyn Heo, Gyeonggi-do (KR); Jin Pyo Chun, Gyeonggi-do (KR)

(73) Assignees: Rayence Co., Ltd., Gyeonggi-do (KR);
VATECH EWOO Holdings Co., Ltd.,
Gyeonggi-do (KR)

( * ) Notice: Subject to any disclaimer, the term of this patent is extended or adjusted under 35 U.S.C. 154(b) by 150 days.

(21) Appl. No.: 14/500,905

(22) Filed: Sep. 29, 2014

(65) Prior Publication Data

US 2016/0038104 A1  Feb. 11, 2016

(30) Foreign Application Priority Data

Aug. 8, 2014  (KR) .................. 10-2014-0102297

(51) Int. Cl.
*A61B 6/14* (2006.01)
*A61B 6/00* (2006.01)

(52) U.S. Cl.
CPC ............. *A61B 6/145* (2013.01); *A61B 6/425* (2013.01)

(58) Field of Classification Search
CPC ......... A61B 6/145; A61B 6/14; A61B 6/4283; A61B 6/4233; A61B 5/4547; G03B 42/042; G03B 42/04
See application file for complete search history.

(56) References Cited

U.S. PATENT DOCUMENTS

| 4,734,034 A | 3/1988 | Maness et al. |
| 4,856,993 A | 8/1989 | Maness et al. |
| 6,042,267 A * | 3/2000 | Muraki ................ G01T 1/2018 348/E5.086 |
| 2003/0031296 A1 | 2/2003 | Hoheisel |
| 2006/0028546 A1 | 2/2006 | Kokkaliaris et al. |
| 2006/0067462 A1 | 3/2006 | Hack |
| 2006/0262461 A1 | 11/2006 | Wood |
| 2007/0053498 A1 * | 3/2007 | Mandelkern .......... G01T 1/2018 378/184 |
| 2009/0034687 A1 * | 2/2009 | Ayraud .................. A61B 6/145 378/168 |
| 2010/0072379 A1 * | 3/2010 | Nishino ................ G01T 1/2018 250/363.08 |

FOREIGN PATENT DOCUMENTS

| EP | 1699232 A2 | 9/2006 |
| JP | 2006-043465 A | 2/2006 |
| JP | 2006-521130 A | 9/2006 |

(Continued)

OTHER PUBLICATIONS

Korean Intellectual Property Office, International Search Report of International Application No. PCT/KR2015/004658, Aug. 13, 2015.

(Continued)

*Primary Examiner* — Hoon Song
(74) *Attorney, Agent, or Firm* — IP Legal Services, LLC

(57) ABSTRACT

Provided is an intraoral sensor including an image sensor configured to bendable and to generate an electrical signal by detecting an X-ray; and a case configured to receive the image sensor and to limits a bending level of the image sensor.

19 Claims, 7 Drawing Sheets

(56) References Cited

FOREIGN PATENT DOCUMENTS

| | | |
|---|---|---|
| JP | 2011-075390 A | 4/2011 |
| JP | 2013-015347 A | 1/2013 |
| KR | 20-0303670 Y1 | 2/2003 |
| KR | 20-0396821 Y1 | 9/2005 |
| KR | 20-2009-0001520 U | 2/2009 |
| KR | 10-2014-0061177 A | 5/2014 |
| KR | 10-2014-0067257 A | 6/2014 |
| WO | 2009/138331 A1 | 11/2009 |

OTHER PUBLICATIONS

Korean Intellectual Property Office, International Search Report of International Application No. PCT/KR2015/008347, Nov. 6, 2015.
Korean Intellectual Property Office, International Search Report of International Application No. PCT/KR2015/008348, Nov. 20, 2015.
Korean Intellectual Property Office, International Search Report of International Application No. PCT/KR2015/008349, Nov. 23, 2015.

\* cited by examiner

INTRAORAL SENSOR

CROSS REFERENCE TO PRIOR APPLICATIONS

The present application claims priority under 35 U.S.C. §119 to Korean Patent Application No. 10-2014-0102297 (filed on Aug. 8, 2014), which is hereby incorporated by reference in its entirety.

BACKGROUND OF THE INVENTION

Field of the Invention

The present invention relates, in general, to an intraoral sensor, and, more particularly, to a bendable X-ray intraoral sensor.

Description of the Related Art

With regard to intraoral radiography for obtaining X-ray images for the teeth and gums in a patient's mouth, a film was commonly used in the past. In the case of such a film, there is a high possibility that image distortion will be generated because the film is excessively bent in a patient's mouth. Further, the films are inefficient in terms of cost and time due to the development of the films and storing them. In order to solve these problems, a digital intraoral sensor has been currently widely used.

Since the digital intraoral sensor is generally composed of components made of a rigid material, the digital intraoral sensor is not bendable. Due to this, it is problematic in that a patient can feel discomfort or even pain due to digital sensor being inserted into his/her mouth.

SUMMARY OF THE INVENTION

An object of the present invention is to provide an intraoral sensor bendable with variable bending level according to a position relation with oral structures such as teeth and peripheral tissues thereof, when the intraoral sensor is inserted into a patient's mouth for taking X-rays images, so that a user's feeling of discomfort or pain can be relieved.

In order to achieve the above object, according to an aspect of the present invention, there is provided a bendable image sensor generating an electrical signal by detecting an X-ray passing through an object to be examined.

In order to achieve the above object, according to another aspect of the present invention, there is provided an intraoral sensor, including a sensing unit generating a electrical signal by detecting the X-ray passing through an object to be examined; and a first case configured for covering a front surface of the sensing unit, wherein the front surface of the sensing unit faces the X-ray. The intraoral sensor may further include a support of rear surface on a center of a rear surface of the sensing unit. The intraoral sensor further may further include a housing configured to cover the first case, a part of the sensing unit, and a part of the support of rear surface. The intraoral sensor may have a shape having a different length in the major axis direction and in the minor axis direction, wherein both end parts of the intraoral sensor in a major axis direction are more easily bendable than a center part of the intraoral sensor. A bending level may be changed according to respective structures in contact with the intraoral sensor in a patient's mouth. A contour surface may be changed according to respective structures in contact with the intraoral sensor in a patient's mouth. The intraoral sensor may further include a support of rear surface on a center of a rear surface of the sensing unit; and a housing configured for the first case, a part of the sensing unit, and a part of the support of rear surface. At least one of the first case and the housing may limit a bending level of the image sensor. The first case may include a base part facing the front surface of the sensing unit; and side walls that protrude from edge sides of the base part so as to cover sides of the sensing unit. The first case may include grooves at the side wall, and wherein distances between the adjacent grooves are reduced gradually from a center part of the side wall toward both end parts. The intraoral sensor may further include a pad portion to which the electrical signals are transmitted at the rear surface of the sensing unit, the support of rear surface may include a body and a contact section provided at the bottom of the body and adhered to the rear surface of the sensing unit, and he intraoral sensor may further comprise a transmission cable electrically connected to the pad portion via the support of rear surface. The intraoral sensor may further include a second case configured to cover the first case and a part of the sensing unit.

In order to achieve the above object, according to further another aspect of the present invention, there is provided an intraoral sensor, including: an image sensor configured to bendable and to generate an electrical signal by detecting an X-ray passing through an object to be examined; and a case configured to receive the image sensor and to limits a bending level of the image sensor. The intraoral sensor may have different lengths in the major axis direction and in the minor axis direction, wherein both end parts of the intraoral sensor in the major direction are more easily bendable than a center part of the intraoral sensor. A bending level of the intraoral sensor is changed according to respective structures in contact with the intraoral sensor in a patient's mouth. A contour surface the intraoral sensor is changed according to respective structures in contact with the intraoral sensor in a patient's mouth.

BRIEF DESCRIPTION OF THE DRAWINGS

The above and other objects, features and other advantages of the present invention will be more clearly understood from the following detailed description when taken in conjunction with the accompanying drawings, in which.

DETAILED DESCRIPTION OF THE INVENTION

Hereinbelow, preferred embodiments of the present invention will be described in detail with reference to the accompanying drawings.

Figure 8A:
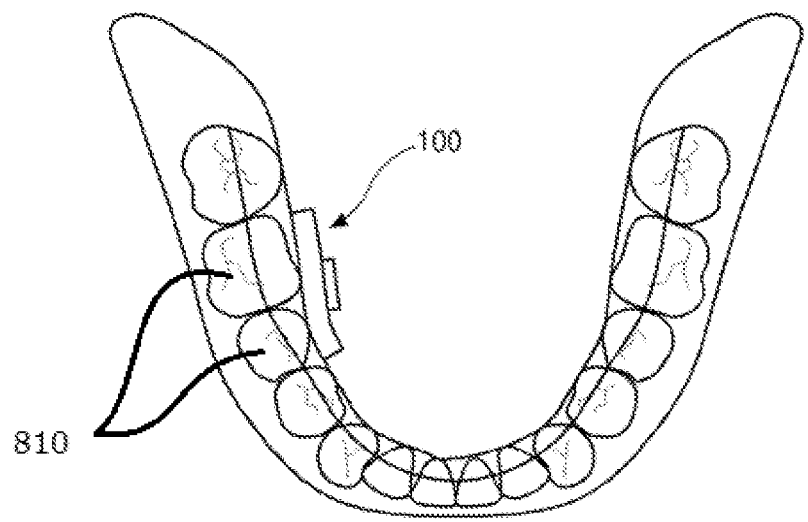
FIGS. 8A and 8B are schematic diagrams for explaining that a contour surface of the intraoral sensor is changed according to each position in a patient's mouth.
Figure 8B:
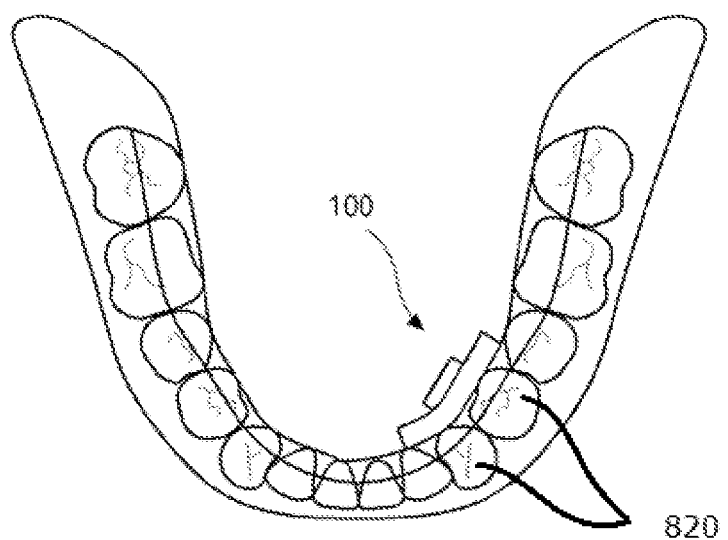

Referring to FIGS. 1 to 4, an intraoral sensor 100 according to an embodiment of the present invention may include: a sensing unit 110 for providing sensitivity information of an X-ray penetrating an object (e.g., objects 810 or 820 of FIG. 8A and FIG. 8B) to be examined as an electrical signal; and a first case 120. The intraoral sensor 100 may further comprise a support of rear surface 180. It is preferable that the first case 120 and the sensing unit 110 be disposed in this order along a direction of the X-ray. Namely, the X-ray may pass the first case 120 and incident to the sensing unit 110. The sensing unit 110 may be configured with a sensing panel or a sensing plate, but not limited thereto, which is bendable.

Figure 3:
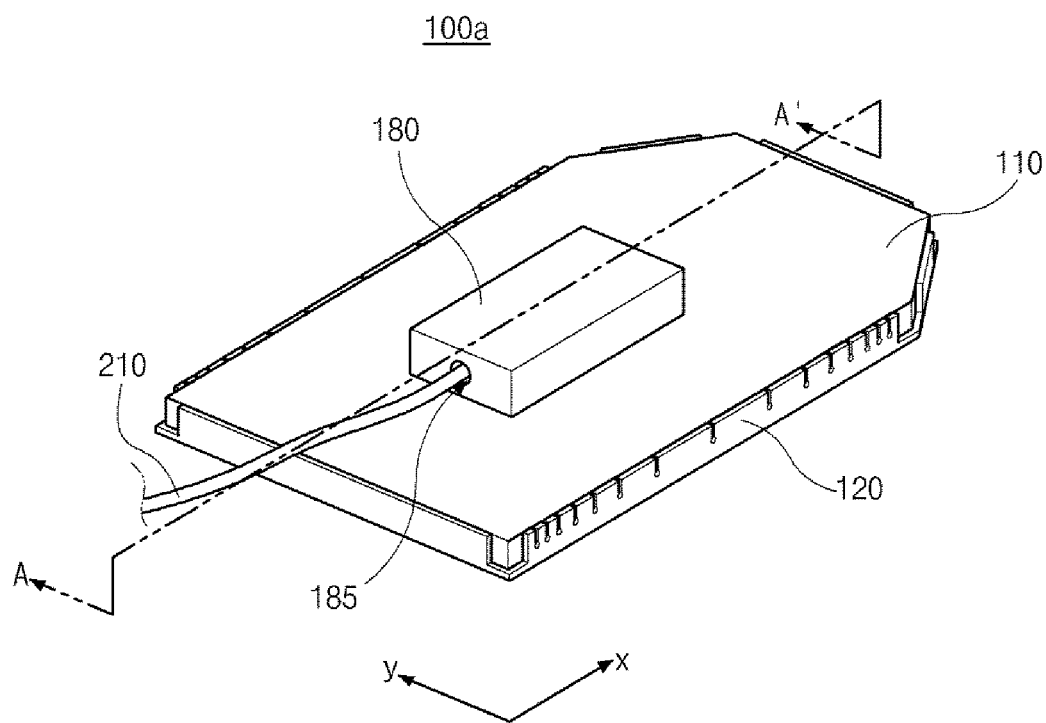
FIG. 3 is a schematic diagram showing a combination of a sensing unit, a first case and a support of rear surface.
Figure 4:
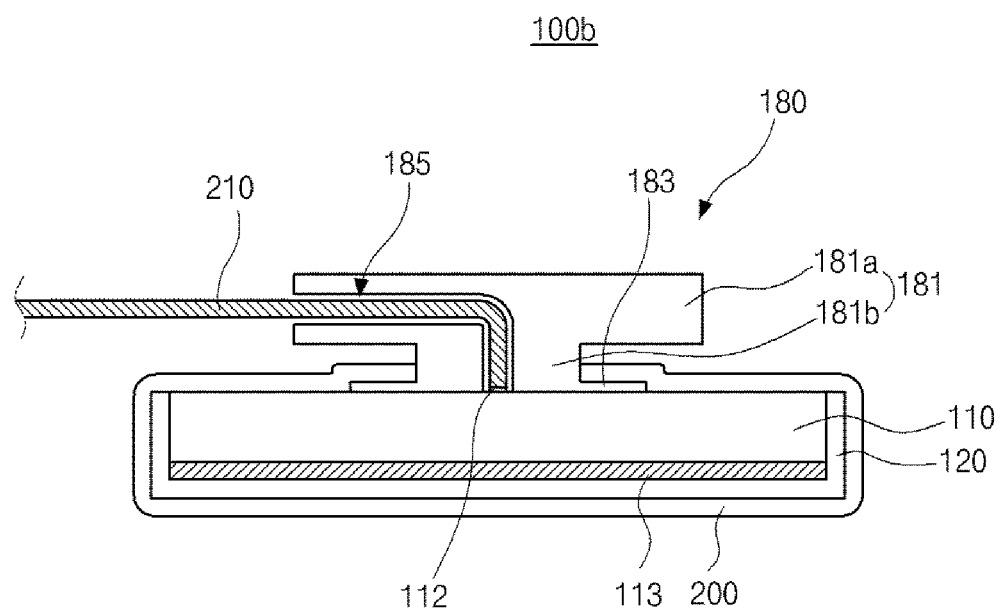
FIG. 4 is a cross-sectional view taken along lines A-A' of the intraoral sensor shown in FIG. 3.

For convenience of the description, FIG. 3 illustrates a structure of the intraoral sensor 100a without a housing 190 and a second case 200, and FIG. 4 illustrates a structure of the intraoral sensor 100b without the housing 190.

The intraoral sensor 100 according to the embodiment of the present invention may include: the sensing unit 110, the first case 120, the support of the rear surface 180, the second case 200 providing an inlet of the support of the rear surface 180, and the housing 190 configured for covering and surrounding the support of the rear surface 180 and the second case 200.

The sensing unit 110 may receive an X-ray at a front surface thereof and may include a plurality of pixels defined in a matrix form along a column direction and a row direction in a service area for obtaining images, namely, in an active area. In the respective pixel, a switching element and a photoelectric conversion element such as a photodiode are formed so that incident light can be converted into an electrical signal and the electrical signal can be transmitted. The switching element may be implemented using a complementary metal-oxide semiconductor (CMOS) transistor or a thin film transistor(TFT). A pad portion 112 intended for outputting the electrical signal to a transmission cable 210 is formed at a region of the rear surface of the sensing unit 110.

In order to realize a bending property of the intraoral sensor 100, the sensing unit 110 also may be configured so as to have a bending property. In case of adopting a brittle substrate of a semiconductor, ceramic, glass and the like as the sensing unit 110, it is preferable that the substrate have a thickness of 100 um or less, and as one example, the substrate may be formed so as to have a thickness of 30 um~70 um, but the thickness is not limited to the ranges. When the substrate is formed in such a thickness, bending strength of the sensing unit 110 may be optimized. In order to form the sensing unit 110 having such a thickness, for example, a method of removing a rear side of the substrate by a predetermined thickness may be used. That is, by applying a grinding process and the like to a rear side of the substrate, which has the photoelectric conversion element and the switching element formed on a front side thereof, the thickness of the substrate may be reduced to the extent as described above.

Figure 5:
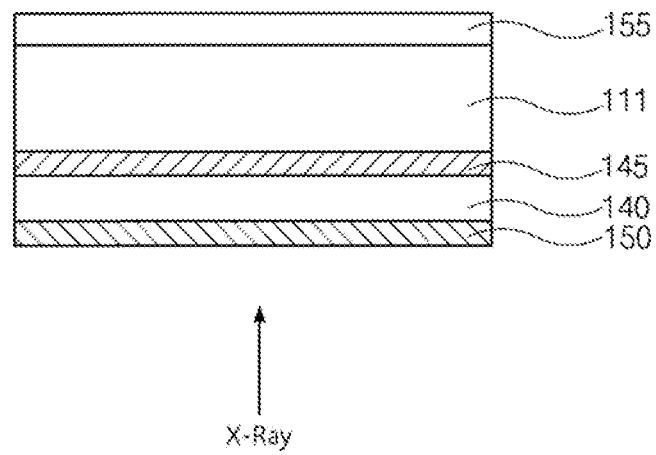
FIG. 5 is a cross-sectional view illustrating a laminate structure for photoelectric conversion of the sensing unit of an indirect conversion mode according to the embodiment of the present invention.

The sensing unit 110 may be a direct conversion sensing unit which directly converts an incident X-ray into an electrical signal. Also, the sensing unit 110 may be an indirect conversion sensing unit which converts an X-ray into a visible ray and converts the visible ray into an electrical signal. When the indirect conversion sensing unit 110 is used, referring to FIG. 5 illustrating a cross-sectional structure 110a of the indirect conversion sensing unit, a scintillator layer 140 intended for converting an X-ray into a visible ray may be provided at a region of a front surface of a substrate 111 of the sensing unit, namely, on a photoelectric conversion element.

As mentioned above, FIG. 5 illustrates an example in which the scintillator layer 140 is formed on an X-ray incident surface in the sensing unit 110. However, as another example, the scintillator layer 40 may be formed on an opposite surface of the X-ray incident surface. One surface of the scintillator layer 140 may be attached to the substrate 111 via an adhesive layer 145. A radiolucent protective layer 150 for protecting the scintillator layer 140 may be formed on the other surface of the scintillator layer 140. The adhesive layer 145 may be formed with a flexible adhesive layer having high light transmittance. For an instance, the adhesive layer 145 may be formed with an optically clear adhesive (OCA) film. A resin film having high radiolucency and a moisture barrier property may be used as the protective layer 150. For reference, the adhesive layer 145 may have a thickness of 10~50 um so as to relieve brittleness of the substrate 111, preferably. In case of using an OCA film as the adhesive layer, the thickness of the adhesive layer 145 may be 15~40 um.

As a scintillating material for forming the scintillator layer 140, for example, CsI or a Gadox ($Gd_2O_2$: Tb) may be used. Since the intraoral sensor 100 according to an embodiment of the present invention is configured so as to have a bending property, it is preferable to use the Gadox scintillator having a corpuscular structure rather than CsI scintillator having a columnar crystal structure. Because of the corpuscular structure of Gadox scintillator, the intraoral sensor will not be easily damaged even if the intraoral sensor 100 is bent. Thus, the generation of defects can be prevented. Moreover, the scintillator layer 140 formed with the Gadox is advantageous in that it is easy to manufacture. For reference, in order to obtain a sufficient amount of light, the scintillator layer 140 formed with the Gadox may have a thickness of 250~500 um, preferably, 300~400 um.

A flexible layer 155 may be formed the other surface of the substrate 111. The flexible layer 155 may be made of, for example, polyimide (PI), and may have a sufficient thickness, for example, a thickness of about 50~150 um, so as to prevent the sensing unit 110 from being damaged when it is bent, by relieving brittleness of the sensing unit 110.

Figure 6:
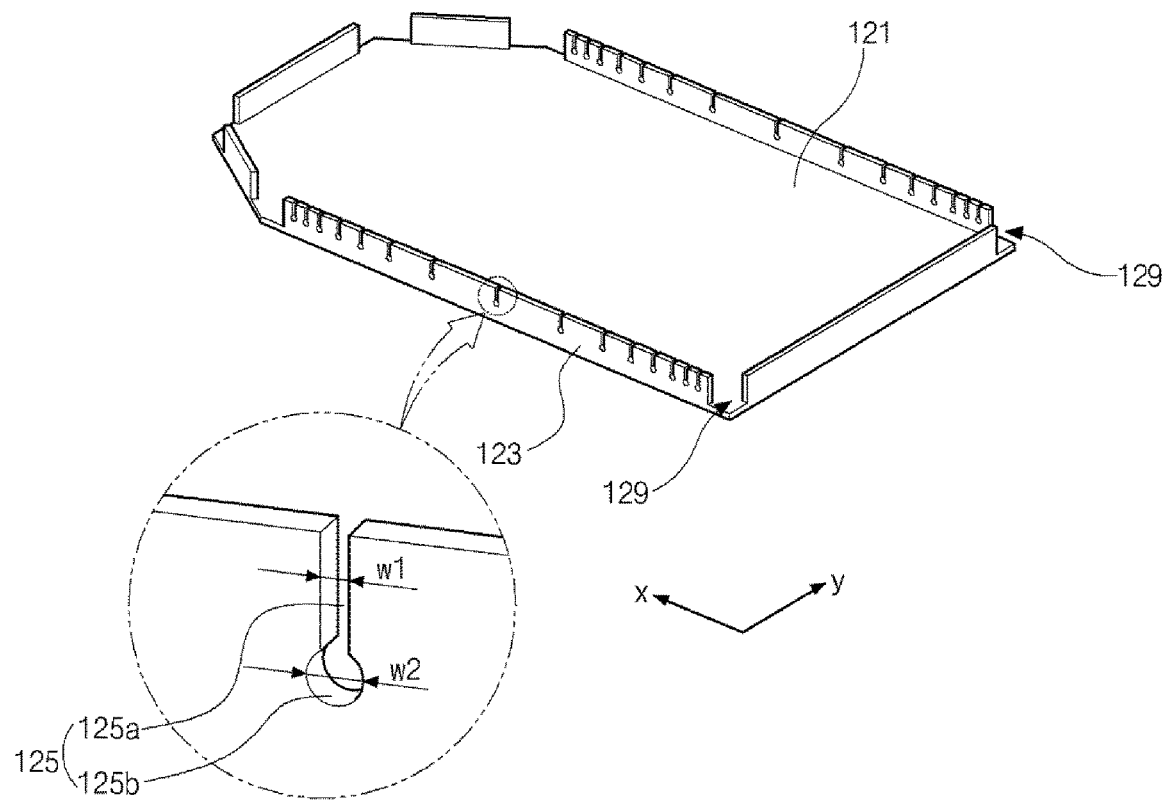
FIG. 6 is a perspective view illustrating a first case according to the embodiment of the present invention.
Figure 7:
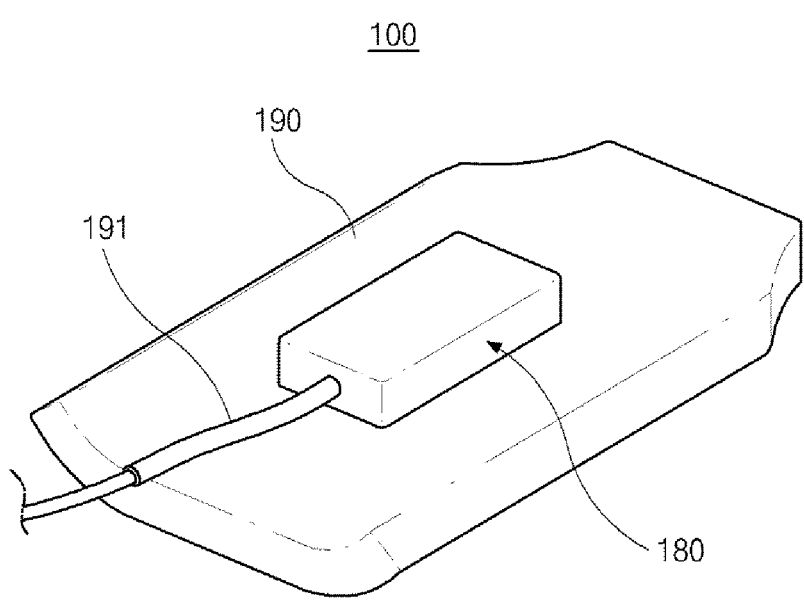
FIG. 7 is a perspective view showing a bendable intraoral sensor according to the embodiment of the present invention.

Referring to FIG. 6 along with FIGS. 1 to 4, the back of the first case 120 has an open box-like shape and the front of the first case 120 faces an X-ray source (not shown) with an object interposed between them. The first case 120 may include a base part 121 and at least one side wall 123. The base part 121 may include a front surface facing the X-ray source and a rear surface facing the front surface of the sensing unit 110. The side wall 123 may be vertically protruded or bent from at least one edge of the base 121 toward the back (inwardly).

The sensing unit 110 may be received in a space formed by the base portion 121 and the side walls 123 of the first case 120. The rear surface of the first case 120 may cover the front surface of the sensing unit 110 so that the sensing unit 110 can be protected from the outside. In particular, the first case 120 according to the embodiment of the present invention may function to limit a bending level of the intraoral sensor 100 according to a material, a shape and the like thereof. The first case 120 may be made of a material having high stiffness while having a bending property. For example, the first case 120 may be made of a flexible glass material or a fiber reinforced plastic (FRP) material, but the material is not limited thereto. The first case 120 may have a thickness of about 0.4 mm, but is not limited thereto. As the first case 120 is made of such a material, bending of the sensing unit 110 may be limited according to a bending level of the first case 120. Thanks to this, the sensing unit 110 may be prevented from being excessively bent and being damaged. Furthermore, the intraoral sensor 100 may be bent within a limited range so that the distortion of images can be minimized.

The base portion 121 may be substantially formed in a rectangular or a hexagonal plane form which have different lengths in the major axis direction and in the minor axis direction. Furthermore, it is preferable that the side walls 123 may be configured not to be formed at every edge of the base portion. The adjacent side walls 123 of edge sides are not connected to each other at respective corner parts and are separated from each other, namely, a gap 129 may be provided between the adjacent side walls 123. As the side walls 123 are not sequentially formed along the entire edge sides of the base portion and the gap 129 is provided in each corner part with which the edge sides meet, the first case 120 can be prevented from being damaged due to a stress concentrated at the respective corner parts of the first case 120 when the intraoral sensor 100 is bent.

The sensing unit 110 may be attached to the rear surface of the base portion 121 of the first case 120 using a soft adhesive layer 113 having radiolucency, for example, a foam tape. The adhesive layer 113 may have a thickness of about 0.2 mm, but is not limited thereto. It is preferable that a height of the side wall 123 of the first case 120 is more than a total thickness of the sensing unit 110 and the adhesive 113 so that the sensing unit 110 can be received in an inner part of the first case 120. The height of the side wall 123 may be about 2.5 mm, but is not limited thereto.

The side walls 123 of the first case 120 may have a plurality of grooves 125 along a longitudinal direction thereof. More specifically, with regard to the first case 120, two side walls 123 facing each other are located along an x-axis direction, which is the major axis direction, and the grooves 125 form in the side walls are configured to correspond to each other. In particular, it is preferable that the grooves 125 is configured such that a distance between the grooves reduces gradually from a center part of the corresponding side wall 123 to both end parts. When these grooves 125 are configured, a bending level may be changed according to each position based on the x-axis direction. That is, as the distance between the grooves 125 becomes narrower, the corresponding part is further bent, and as the distance between the grooves 125 becomes broader, the corresponding part is less bent. Due to this, the first case 120 may have a property in which a bending level increases gradually from the center to both ends with regard to the x-axis direction. Such a bending property is provided to the intraoral sensor 100. Like this, as the bending property is adjusted according to each position, a patent's discomfort generated upon taking an X-ray in his/her mouth can be more effectively reduced. Most of both end parts of the intraoral sensor in the major axis direction are more easily in contact with tissues in the patient's mouth compared with a center part of the intraoral sensor 100, thereby causing a pain at the ends of the intraoral sensor. In the embodiment of the present invention, both end parts of the intraoral sensor 100 in the major axis direction are configured to be more easily bent than the center part of the intraoral sensor 100 so that the patient's discomfort can be more relieved. Also, the intraoral sensor 100 is gradually less bent at the center part thereof, and the overall distortion of an image due to bending can be minimized.

The grooves 125 formed at the side walls 123 are configured to cross a longitudinal direction of the side walls 123. The grooves 125 are vertical to the longitudinal direction of the side walls 123 or the grooves 125 may have a slope at a predetermined angle with respect to the longitudinal direction of the side walls 123. For convenience sake, the grooves 125 may be extended from a top to a bottom of the side wall 123 and may include a first groove portion 125a substantially having a predetermined first width w1 and a second groove portion 125b located under the first groove portion 125a. At least a part of the second groove portion 125b may be configured so as to have a second width w2 which is wider than the first width w1 of the first groove portion 125a.

The second groove portion 125b may have various shapes. In the embodiment of the present invention, the second groove portion 125b may have a full circle-like shape. As the second groove portion 125b of the side wall 123 is formed to have a wider width w2, a bottom part of the grooves 125 of the side wall 123 may be prevented from being damaged when the intraoral sensor 100 is bent, and the first case 120 may be further bent because the grooves 125 may be further open when the intraoral sensor 100 is bent.

Even though as an example, the aforesaid embodiment shows a case in which the grooves 125 are formed at the side wall 123 of the major axis direction, the grooves 125 may be also formed at the side wall 123 of a minor axis direction as needed, and a distance between the adjacent grooves 125 may be adjusted.

The support of rear surface 180 may be positioned at the rear of the sensing unit 110 and is in contact with the user's finger or is connected to an instrument in order to support the intraoral sensor 100 while an X-ray image of a patient's tooth or peripheral tissues in mouth is being taken. Referring to FIG. 4, the support of rear surface 180 may include: a body 181; a contact section 183 located at a lower part of the body 181 and connected to the body 181, the contact section 183 extending to an outer side and having a plate shape; and an inlet 185 passing through the support of rear surface 180 from one side of the body 181 to the contact section 183. This support of rear surface 180 may be formed using a molding method and thus may be integrally configured, but is not limited thereto.

The body 181 is composed of an upper portion 181a and a lower portion 181b located below the upper portion and formed inwardly. As a width of the upper portion 181a is formed wider than that of the lower portion 181b, a side of the support of rear surface 180 may have a step.

The contact section 183 is connected to the lower portion 181b of the body 181, and is located to correspond to the center part of the sensing unit 110. A front surface of the contact section 183 is adhered to the rear surface of the sensing unit 110 so as to support the rear of the sensing unit 110. Accordingly, a bending level of the center part of the sensing unit 110 may be limited by the contact section 183.

The intraoral sensor has a property such that a center part of the intraoral sensor 100 corresponding to the contact section 183 is less bent than peripheral parts of the intraoral sensor which are relatively more bent, so that a patent's discomfort can be relieved and the distortion of images can be also minimized. Like this, a bending level of the intraoral sensor 100 may be limited by the contact section 183 and may be also adjusted according to each position of the intraoral sensor.

A transmission cable 210 is inserted into the inlet 185. One end of the inlet 185 may be extended from one side of the body 181, and the other end of the inlet 185 is configured to be located at the bottom of the contact section 183. Here, the other end of the inlet 185 is located to correspond to the pad portion 112 of the sensing unit 110.

The transmission cable 210 inserted into the inlet 185 may be electrically connected to the pad portion 112 of the sensing unit 110 at the other end of the inlet 185. An anisotropic conducting film (ACF), wire bonding, soldering and the like may be used for the electrically connection of the transmission cable 210 and the pad portion 112.

The contact section 183 is adhered to the rear surface of the sensing unit 110 so that the rear of the intraoral sensor can be supported, and the electrical connection between the transmission cable 210 and the sensing unit 110 may be stably realized.

The sensing unit 110, the first case 120 arranged at the front of the sensing unit 110, and the support of rear surface 180 of the sensing unit 110 are combined. In order to further strengthen the combination of these elements, the second case 200 may be adopted. The second case 200 may be a mold case. Referring to FIG. 4, the second case 200 may be formed to cover the front surface and the side walls of the first case 120, the rear surface of the sensing unit 110, and a rear surface of the contact section 183. It is preferable that the second case 200 may be formed to have a predetermined thickness from the rear surface of the contact section 183 of the support of rear surface 180 in order to cover a side of the lower portion 181b of the body 181. The second case 200 may be formed to expose the remaining parts, i.e., the support of rear surface 180 except a part of the lower portion 181b.

It is preferable that the second case 200 may be made of, for example, a resin material cured by UV rays. In particular, in consideration of a bending property shown in a limited range, it is preferable that a material having a shore hardness of about D 10~20 be used as a material for the second case 200.

As such, as the second case 200 is provided, the sensing unit 110, the first case 120 and the support of rear surface 180 may be more stably combined with each other, and the electrical connection between the sensing unit 110 and the transmission cable 210 may be more stably fixed. When the second case 200 is made of a material having a bending property within a limited range, an entire bending level of the intraoral sensor 100 may be limited according to a purpose.

Figure 1:
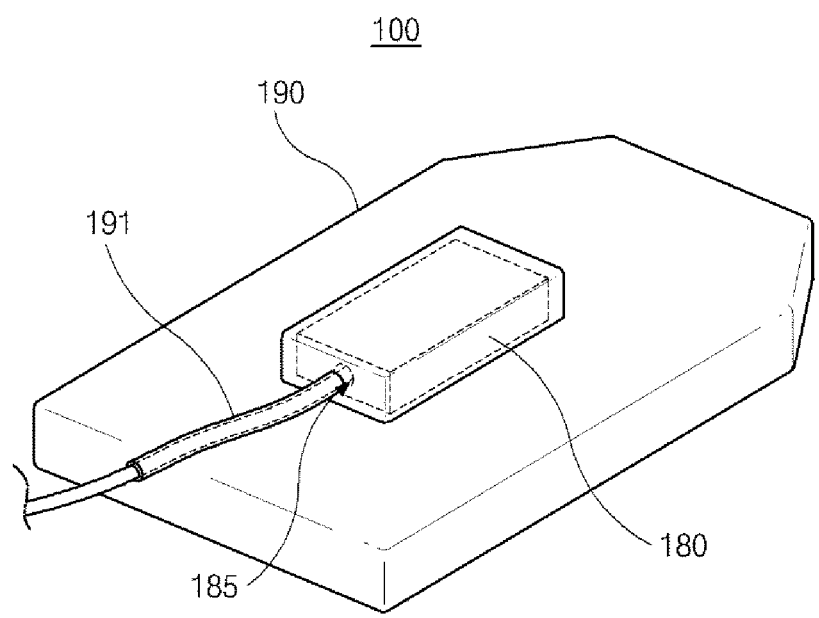
FIG. 1 is a perspective view of an intraoral sensor according to an embodiment of the present invention.
Figure 2:
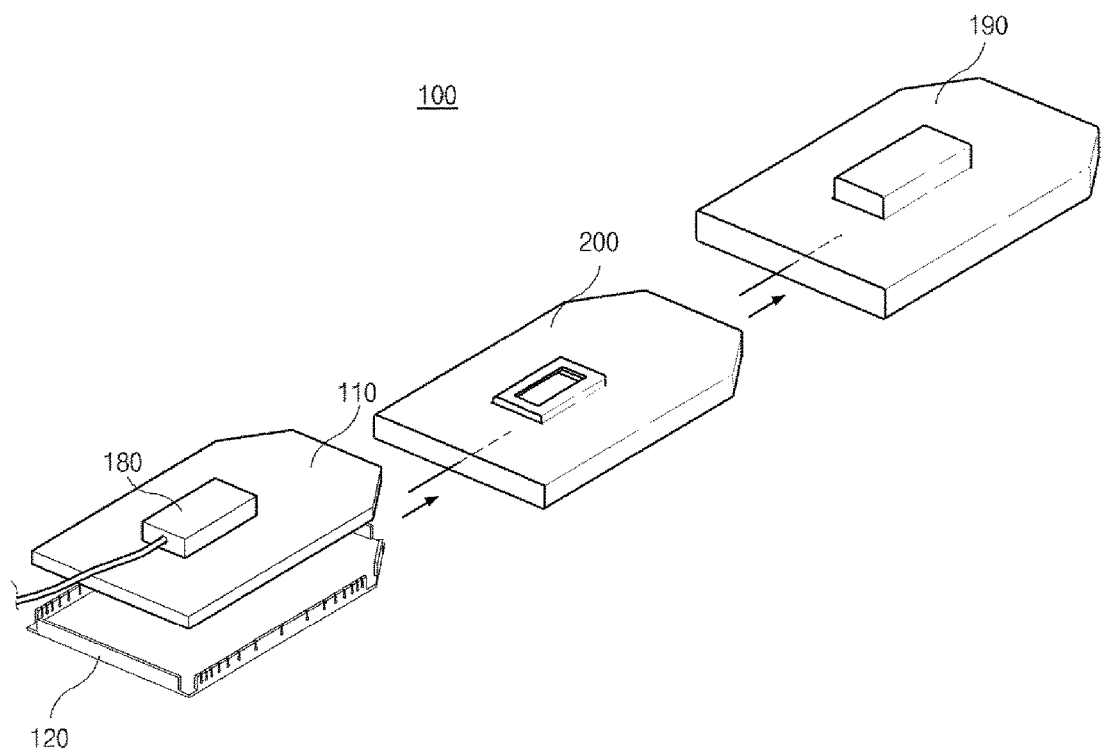
FIG. 2 is an exploded perspective view of the intraoral sensor according to the embodiment of the present invention of FIG. 1.

As such, by applying a molding process to the intraoral sensor 100 having the second case 200, the intraoral sensor 100, which is configured such that an entire outer surface thereof, with the exception of a part of the support of rear surface 180, is covered by the housing 190 as shown in FIG. 1, may be manufactured. The housing 190 may function to surround and protect an outer surface of the intraoral sensor 100. It is preferable that the housing 190 be configured to entirely cover the second case 200. In case of omitting the second case 200, the molding process may be applied to the intraoral sensor 100 having the first case 120. Thus, the housing 190 is configured to surround both an outer surface of the first case 190 and the rear of the sensing unit 110. In this embodiment of the present invention, where the second case 200 is not be provided, the electrical connection between the transmission cable 210 and the intraoral sensor 100 by the mold housing 190 may be also stably performed.

The housing 190 may be configured to fill at least a part of the inlet 185 of the support of rear surface 180. For example, as shown in FIG. 1, the housing 190 may be configured to cover one end of the inlet 185 located at one side of the body 181. Also, with regard to the transmission cable 210 extending from the inlet 815 to the outside, the housing 190 may be extended to surround a part of the transmission cable 210 up to a predetermined length from one end of the inlet 185. That is, the housing 190 may include an extension portion 191 which surrounds the transmission cable 210.

When a part of the transmission cable 210 extending from the inlet 185 to the outside is covered by a sheath made of a resin material or the like as that of the housing 190, this sheath may be surrounded by the extension portion 191. The sheath may extended up to a connection part between the transmission cable 210 and the sensing unit 110. That is, in the transmission cable 210, a partial length of the transmission cable 210, which goes through the inlet 185 to the connection part of the sensing unit 110, may be covered by the sheath.

When the housing 190 and the sheath are made of the same kind of a material, a bonding property of the housing and the sheath is improved, and as a result, a connection of the transmission cable 210 and the intraoral sensor can be more stabilized.

In the embodiment of the present invention, the housing 190 may be made of a material having a soft property, for example, silicone or urethane. In particular, it is preferable that a material having a shore hardness of about A 30~50 may be used as the soft material constituting the housing 190.

As described above, when the housing 190 having a soft property is used, a pain inflicted to a patent may be considerably relieved when an X-ray image of teeth or peripheral tissues in his/her mouth is taken. That is, as the housing 190, which is formed with the molding process and the outermost element of the intraoral sensor 100 being in direct contact with a tissue in the mouth, is provided with a soft property, the patient feels comfort upon being in contact with the intraoral sensor 100 so that a pain can be effectively relieved. In consideration of this property, it is preferable that the intraoral sensor 100 covered by the housing 190 has a thickness of about 5 mm except for the support of rear surface 180, but is not limited thereto.

The intraoral sensor 100 having the configuration as described above is bendable when the intraoral sensor 100 is inserted into the patent's mouth for taking an X-ray image of structures in the his or her mouth, namely, teeth and peripheral tissues. Furthermore, a contour surface of the intraoral sensor may be changed according to each position of the intraoral sensor in a patient's mouth, and this may be referred to by FIGS. 8A and 8B. A bending level of the intraoral sensor 100 may be changed according to positions due to a supporting force applied toward the structures in the patient's mouth and a repulsive force by the structures. The bending level of the intraoral sensor 100 may be changed according to an arrangement relation between the intraoral sensor 100 and each position of the structures in the mouth within an elastic limit. Accordingly, the feeling of discomfort and a pain inflicted to the patient, are largely reduced, and a possibility of image distortion will be low.

As described above, the intraoral sensor according to the embodiment of the present invention adopts the first case bendable within a limited range to receive the sensing unit at the front. Accordingly, the intraoral sensor is bendable within a limited range, thereby the X-ray intraoral sensor which is bendable, without causing distortion to be considered and pain inflicted to the patient.

Moreover, as a bending property is adjusted according to a position by forming grooves at the side walls of the first case, the distortion of images can be minimized when the X-ray image of a patient's mouth is taken, and the patient's discomfort can be more effectively relieved.

Also, as the support of rear surface is formed on the rear of the sensing unit, a bending level of the center part of the sensing unit pressed by the support of rear surface is limited compared with that of the peripheral part of the sensing unit so that the distortion of images can be minimized, and the patient's discomfort can be relieved.

Also, as a combination of the elements of the intraoral sensor is more firmly performed using the second case formed with a mold method, an electrical connection between the transmission cable and the intraoral sensor can be stably performed.

Also, as an outer part of the intraoral sensor is covered by a housing having a soft property, discomfort experienced by the patient can be considerably reduced.

Consequently, according to the embodiments of the present invention, the intraoral sensor having a bending property within a limited range and capable of minimizing the distortion of images can be effectively configured. In addition, an electrical connection portion between the transmission cable and the intraoral sensor can be stably protected, and the patient's discomfort can be reduced.

Although a preferred embodiment of the present invention has been described for illustrative purposes, those skilled in the art will appreciate that various modifications, additions and substitutions are possible, without departing from the scope and spirit of the invention as disclosed in the accompanying claims.

What is claimed is:

1. An intraoral sensor, comprising:
   a sensing unit configured to detect an X-ray passing through an object to be examined and generate an electrical signal based on the detected X-ray, wherein the sensing unit includes i) a front surface facing the object and receiving the X-ray passing through the object and ii) a rear surface having a support; and
   a first case configured to cover the front surface and sides of the sensing unit,
   wherein the first case includes:
      a base contacting and covering the front surface of the sensing unit; and
      four side walls covering corresponding sides of the sensing unit, and
   wherein at least one of the four side walls include a plurality of grooves for allowing the first case to be bended and for limiting a bending degree of the first case.

2. The intraoral sensor of claim 1, wherein the support disposed on a center of the rear surface of the sensing unit.

3. The intraoral sensor of claim 1, further comprising:
   a housing configured to cover the first case, a part of the sensing unit, and a part of the support.

4. The intraoral sensor of claim 1, wherein the intraoral sensor has a shape having a different length in a major axis direction and in a minor axis direction, wherein both end parts of the intraoral sensor in the major axis direction are more easily bendable than a center part of the intraoral sensor.

5. The intraoral sensor of claim 1, wherein a bending level of the intraoral sensor is changed according to a shape of the object in contact with the intraoral sensor.

6. The intraoral sensor of claim 1, wherein a shape of the intraoral sensor is changed along the object contacting the intraoral sensor.

7. The intraoral sensor of claim 1, wherein at least one of the first case and the housing limits a bending level of the image sensor.

8. The intraoral sensor of claim 1, wherein:
   the intraoral sensor further comprises a pad portion to which the electrical signals are transmitted at the rear surface of the sensing unit;
   the support includes a body and a contact section provided at a bottom of the body and adhered to the rear surface of the sensing unit; and
   the intraoral sensor further comprises a transmission cable electrically connected to the pad portion via the support.

9. The intraoral sensor of claim 1, further comprising a second case configured to cover the first case and a part of the sensing unit.

10. An intraoral sensor, comprising:
    an image sensor configured to be bendable, to detect an X-ray passing through an object to be examined, and to generate an electrical signal based on the detected X-ray; and
    a case configured to receive the image sensor and to limits a bending level of the image sensor,
    wherein the image sensor includes i) a front surface facing the object and receiving the X-ray passing through the object and ii) a rear surface having a support,
    wherein the case includes:
       a base contacting and covering the front surface of the sensing unit; and
       four side walls covering corresponding sides of the sending unit, and
    wherein two side walls facing each other include at least one groove for limiting a bending level of the sensing unit.

11. The intraoral sensor of claim 10, wherein the intraoral sensor has different lengths in a major axis direction and in a minor axis direction, wherein both end parts of the intraoral sensor in the major direction are more easily bendable than a center part of the intraoral sensor.

12. The intraoral sensor of claim 10, wherein a bending level of the intraoral sensor is changed according to the object contacting the intraoral sensor.

13. The intraoral sensor of claim 10, wherein the intraoral sensor is bended along a surface of the object, which contacts the intraoral sensor.

14. The intraoral sensor of claim 1, wherein the plurality of grooves are formed on at least one of the four side walls in a predetermined pattern for allowing the first case to be bended to one direction and for limiting a bending level of the first case.

15. The intraoral sensor of claim 1, wherein a number of grooves formed in a middle of each side wall is greater than a number of grooves formed in both ends of each side wall.

16. The intraoral sensor of claim 1, wherein each groove of the plurality of grooves has a predetermined shape to allow the first case to be bended in one direction along a contacting side of the object.

17. The intraoral sensor of claim 1, wherein:
    each groove of the plurality of grooves includes a bottom opening portion and a top opening portion; and
    a width of the bottom opening portion is different from that of the top opening portion.

18. The intra oral sensor of claim 1, wherein:
    the bottom opening has a circular shape; and
    the top opening has a rectangular shape.

19. The intra oral sensor of claim 1, wherein the first case includes at least one gap disposed between two adjacent side walls of the four side walls.

* * * * *